(12) United States Patent
Wolford et al.

(10) Patent No.: US 7,217,271 B2
(45) Date of Patent: May 15, 2007

(54) ORTHOPAEDIC REAMER DRIVER FOR MINIMALLY INVASIVE SURGERY

(75) Inventors: Todd A. Wolford, Goshen, IN (US); Mark Nordman, Burket, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 419 days.

(21) Appl. No.: 10/659,812

(22) Filed: Sep. 11, 2003

(65) Prior Publication Data

US 2004/0097947 A1  May 20, 2004

Related U.S. Application Data

(60) Provisional application No. 60/410,648, filed on Sep. 13, 2002.

(51) Int. Cl.
*A61B 17/00* (2006.01)

(52) U.S. Cl. ..................................................... 606/80

(58) Field of Classification Search ................ 606/79, 606/80, 81, 170, 180
See application file for complete search history.

(56) References Cited

U.S. PATENT DOCUMENTS

| | | | |
|---|---|---|---|
| 3,702,611 A * | 11/1972 | Fishbein | 606/81 |
| 4,023,572 A | 5/1977 | Weigand et al. | |
| 4,834,092 A | 5/1989 | Alexson et al. | |
| 5,169,401 A | 12/1992 | Lester et al. | |
| 5,171,312 A | 12/1992 | Salyer | |
| 5,501,686 A * | 3/1996 | Salyer | 606/79 |
| 5,536,271 A | 7/1996 | Daly et al. | |
| 5,571,200 A | 11/1996 | Cohen et al. | |
| 5,643,271 A | 7/1997 | Sederholm et al. | |
| 5,658,290 A * | 8/1997 | Lechot | 606/80 |
| 5,817,096 A * | 10/1998 | Salyer | 606/81 |
| 5,976,144 A * | 11/1999 | Fishbein et al. | 606/80 |
| 6,283,971 B1 * | 9/2001 | Temeles | 606/81 |
| 2003/0212402 A1 | 11/2003 | White et al. | |
| 2005/0049601 A1 * | 3/2005 | Keller | 606/81 |

* cited by examiner

*Primary Examiner*—Eduardo C. Robert
*Assistant Examiner*—James L. Swiger
(74) *Attorney, Agent, or Firm*—Taylor & Aust, P.C.

(57) ABSTRACT

An orthopaedic reamer assembly for minimally invasive surgery including a reamer and a driver. The driver includes a shaft with a distal end and a longitudinal axis; and a driver head connected to the distal end. The driver head is pivotable about an axis generally perpendicular to the longitudinal axis. The reamer is connected to the driver head.

13 Claims, 8 Drawing Sheets

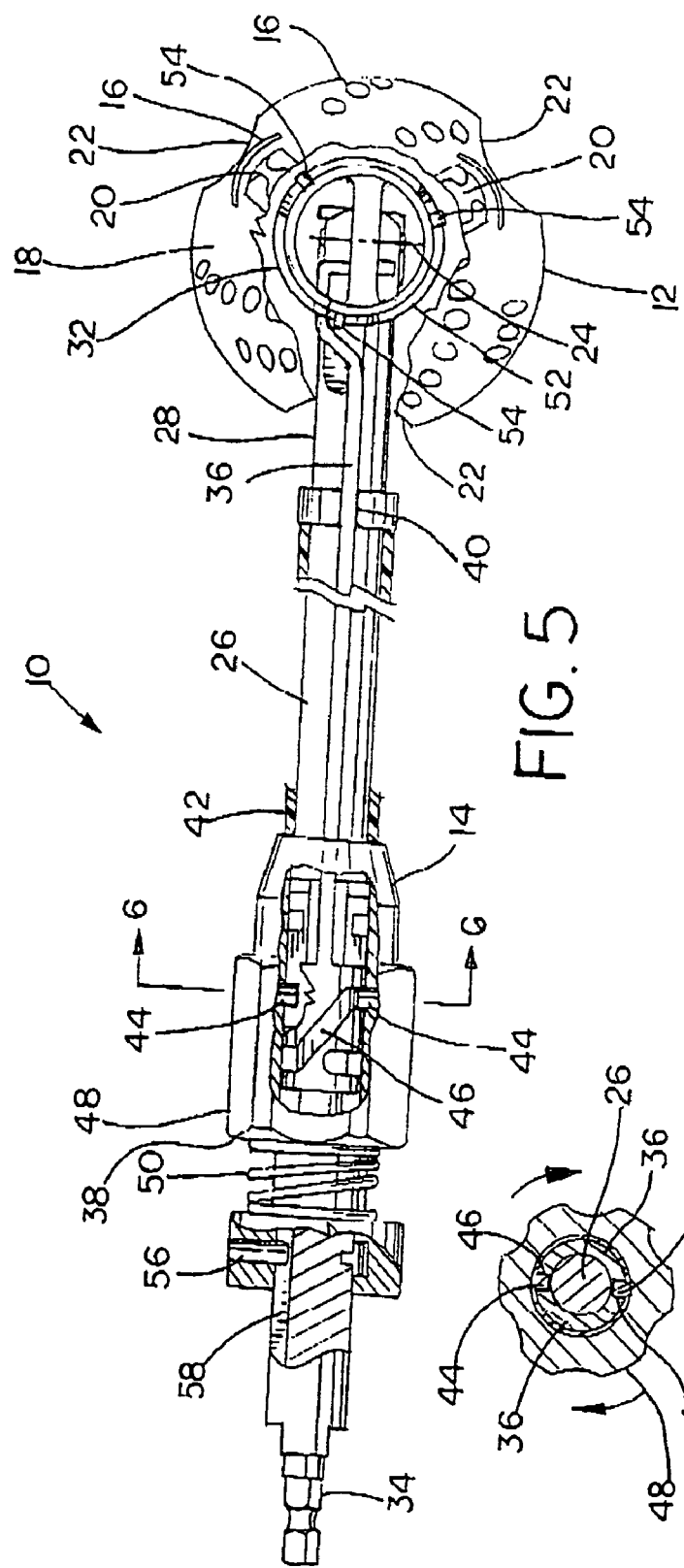

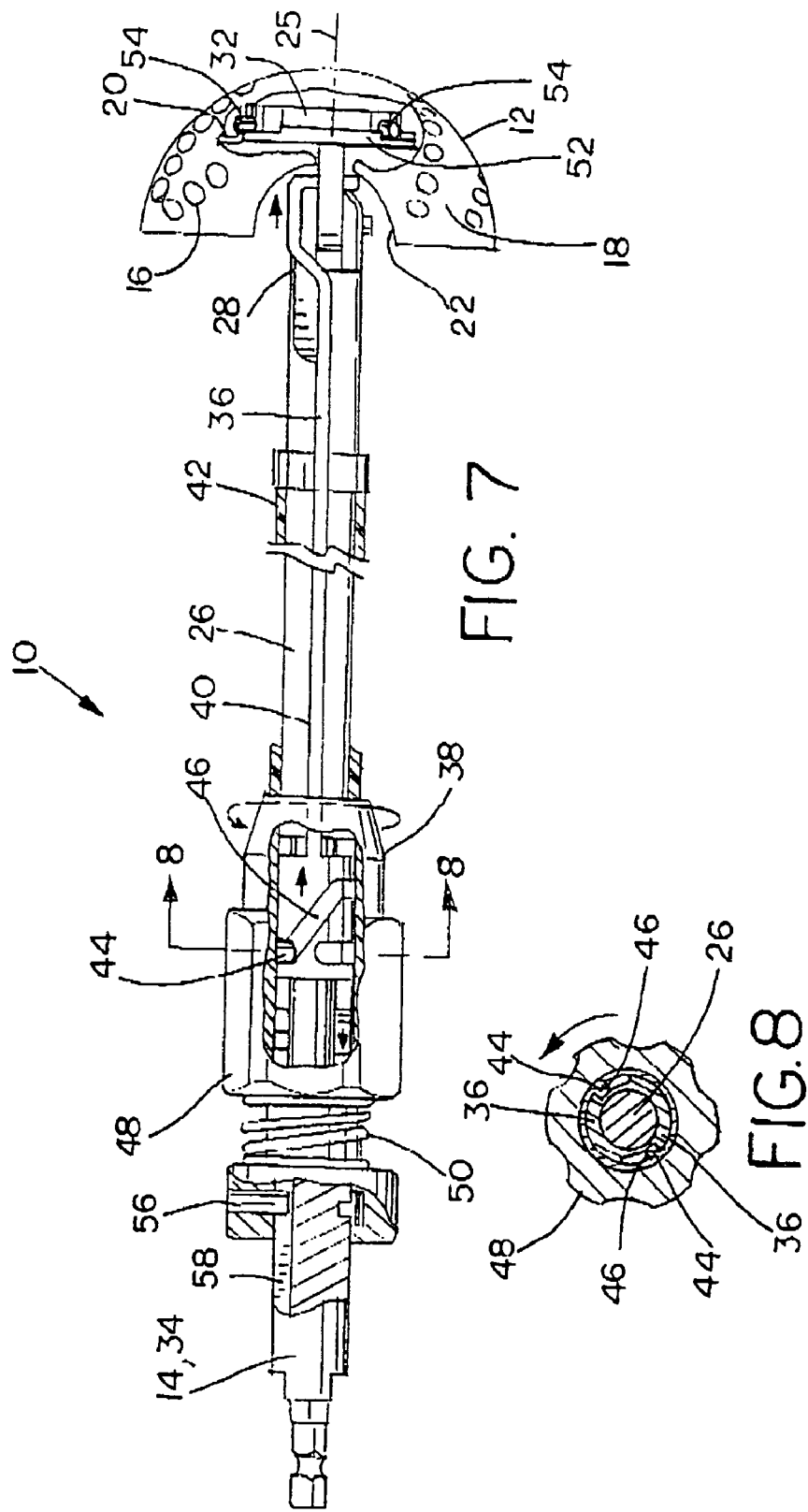

ORTHOPAEDIC REAMER DRIVER FOR MINIMALLY INVASIVE SURGERY

CROSS REFERENCE TO RELATED APPLICATIONS

This is a non-provisional application based upon U.S. provisional patent application Ser. No. 60/410,648, entitled "ACETABULAR REAMER DRIVER FOR MINIMALLY INVASIVE SURGERY", filed Sep. 13, 2002.

BACKGROUND OF THE INVENTION

1. Field of the Invention

The present invention relates to orthopaedic reamer assemblies, and, more particularly, to drivers used with orthopaedic reamer assemblies.

2. Description of the Related Art

The small incision that surgeons are using for minimally invasive hip surgery make it difficult to insert a current full size hemispherical acetabular reamer through the small incision. However, the full size hemispherical acetabular reamer cuts a full hemispherical shape in the acetabulum with minimal wobbling and therefore provides an excellent preparation for the hip joint prosthesis.

Orthopaedic reamers are known that cut off opposing segments of the hemispherical shell of the reamer. The resulting reamer, while having a reduced profile in a certain orientation, is no longer rotationally symmetric. The lack of rotational symmetry can cause vibration and wobbling of the reamer when in use. Such a cut-down reamer design can cut an irregular cavity in the acetabulum, for example, during hip joint prosthesis. An irregular cavity in the acetabulum can reduce the expected lifetime of the hip joint prosthesis, cause discomfort for the patient and increase the wear in the artificial joint, among other problems.

An expanding reamer is known for surgical reaming of the acetabulum in hip surgery. The reamer includes a head with a convex end adapted to seat in a previously prepared concavity in the central part of the acetabulum. This head pivotably mounts a set of radially expansive blades. The reamer is telescopically mounted on the end of a rotary drive shaft, and the drive shaft mounts a cam actuator which engages cam elements to expand the cutters progressively in response to axial thrust exerted on the drive shaft by a surgeon with the reamer head seated in the acetabulum. A spring is used to contract the cutters when the reaming operation is interrupted. Such a reamer has many moving parts associated therewith, adding to the cost of the reamer, making the reamer difficult to clean and sterilize and reducing the reliability of the reamer.

What is needed in the art is a device and method for using a full size hemispherical acetabular reamer, of a reliable design, in minimally invasive hip surgery consistent with the small incision thereof.

SUMMARY OF THE INVENTION

The present invention provides a orthopaedic reamer assembly with a reamer which rotates about an axis transverse to the driver longitudinal axis.

The invention comprises, in one form thereof, a reamer and a driver. The driver includes a shaft with a distal end and a longitudinal axis; and a driver head connected to the distal end. The driver head is pivotable about an axis generally perpendicular to the longitudinal axis. The reamer is connected to the driver head.

An advantage of the present invention is a device and method for using a full size hemispherical acetabular reamer in minimally invasive hip surgery consistent with the small incision thereof.

Another advantage of the present invention is an orthopaedic reamer assembly that rotates a reamer to reduce the reamer profile for a surgical incision.

Yet another advantage of the present invention is a device and method that returns the reamer to an operational position after insertion into a surgical incision.

A further advantage of the present invention is an orthopaedic reamer assembly that rotates a reamer to reduce the reamer profile when withdrawing from a surgical incision.

A yet further advantage of the present invention an orthopaedic reamer assembly for minimally invasive surgery that does not complicate the reamer design.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 5 is a partially fragmentary side view of an embodiment of the orthopaedic reamer assembly of the present invention shown with the reamer in a folded (insertion or retraction) position;

FIG. 6 is a section view of the orthopaedic reamer assembly of FIG. 5 taken along section line 6—6;

FIG. 7 is a partially fragmentary side view of an embodiment of the orthopaedic reamer assembly of the present invention shown with the reamer in a cutting mode (operational) position;

FIG. 8 is a section view of the orthopaedic reamer assembly of FIG. 7 taken along section line 8—8;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
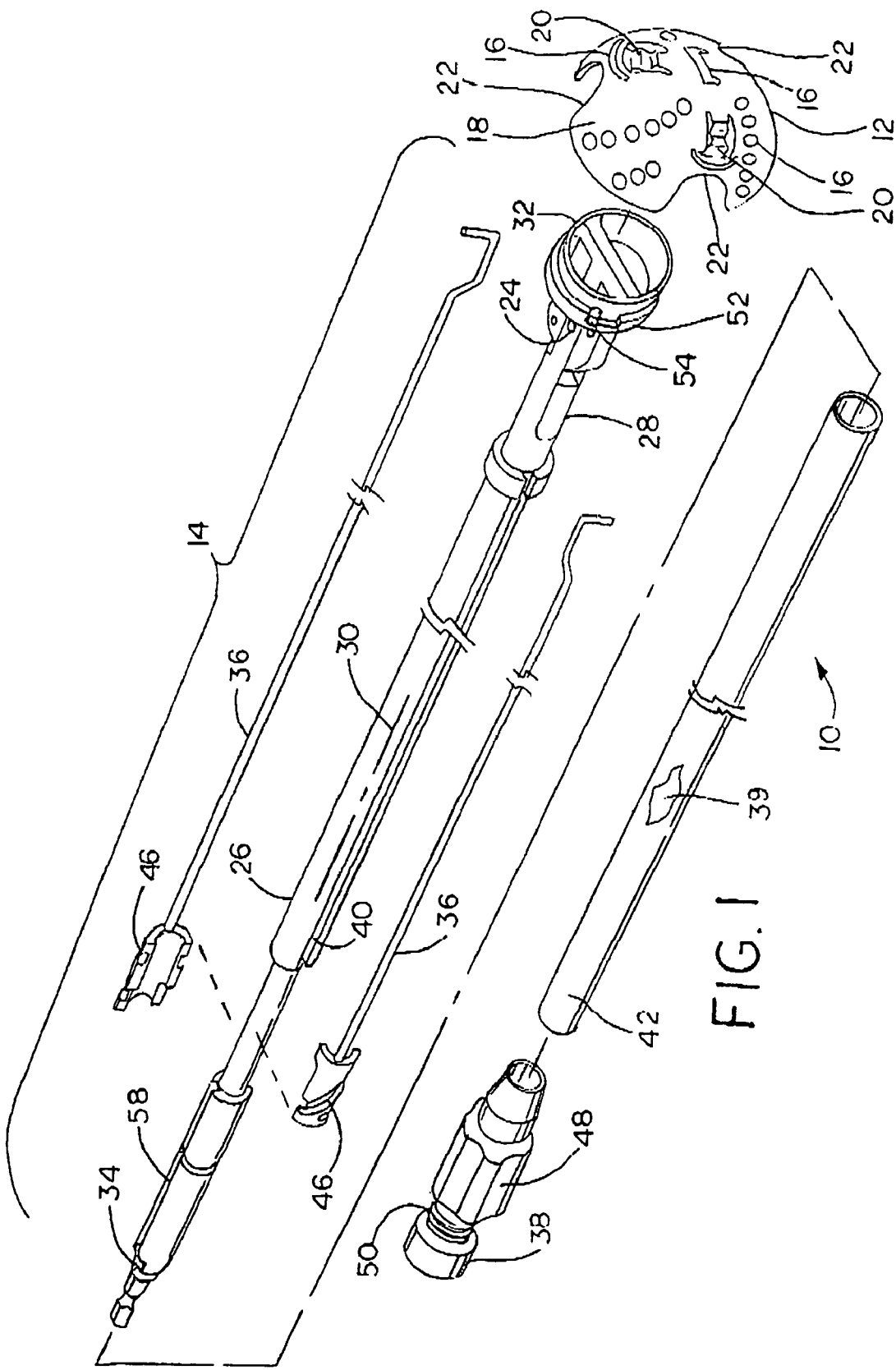
FIG. 1 is an exploded perspective view of an embodiment of the orthopaedic reamer assembly of the present invention.

Referring now to the drawings, and more particularly to FIG. 1, there is shown an orthopaedic reamer assembly 10, which generally includes reamer 12 and driver 14.

Figure 9:
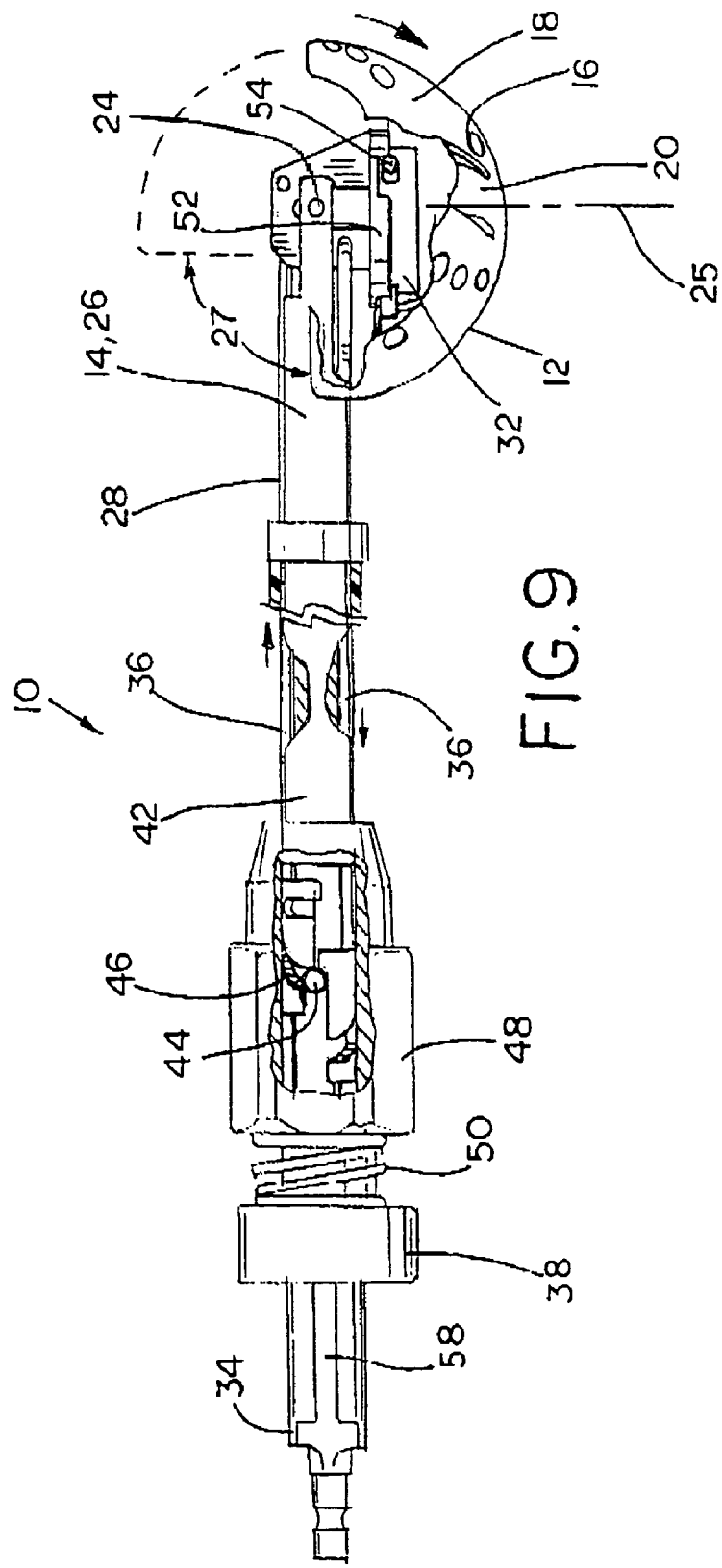
FIG. 9 is a partially fragmentary top view of an embodiment of the orthopaedic reamer assembly of the present invention shown with the reamer in a folded (insertion or retraction) position.
Figure 10:
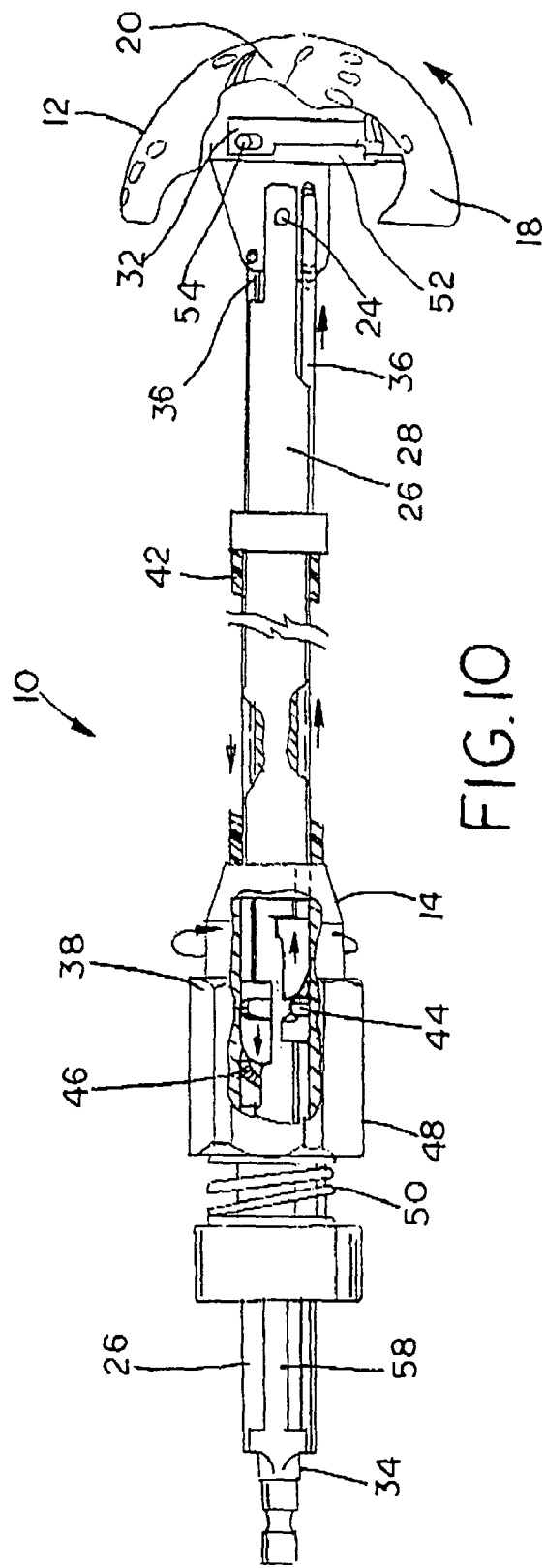
FIG. 10 is a partially fragmentary side view of an embodiment of the orthopaedic reamer assembly of the present invention shown with the reamer in a cutting mode (operational) position.

Reamer 12 includes cutting teeth 16 in hemispherical shell 18. Cutting teeth 16 can be of a variety of shapes and sizes, and are located to provide a generally full hemispherical cutting coverage. Hemispherical shell 18 further includes attachment elements 20 for connecting to driver 14. Cutouts 22 in hemispherical shell 18 allow reamer 12 to rotate over driver 14. Reamer 12 has pivot axis 24 that can be transverse and/or generally perpendicular to the longitudinal axis of driver 14. Pivot axis 24 can extend through the longitudinal axis of driver 14. Rotation axis 25 of reamer 12 is pivotable through a predefined angle 27 (FIG. 9), which can be approximately 90°, but can also be greater than or less than 90°. Predefined angle 27 can be subtended by rotation axis 25 parallel to longitudinal axis 30 and rotation axis 25 transverse to longitudinal axis 30. Rotation axis 25 can also extend through longitudinal axis 30.

Driver 14 includes shaft 26 with distal end 28 and longitudinal axis 30. Driver head 32 is connected to distal end 28. Driver head 32 is pivotable about pivot axis 24. Reamer 12 is connected to driver head 32. Proximal end 34 of shaft 26 connects to a rotating tool (not shown). Driver 14 further includes rods 36 that connect at one end to driver head 32 and another end to chuck 38. Shaft 26 can have longitudinal grooves 40 for rods 36. Tube 42 at least partially covers shaft 26 and rods 36, and can include indicia 39 showing proper actuation of orthopaedic reamer assembly 10.

Figure 2:
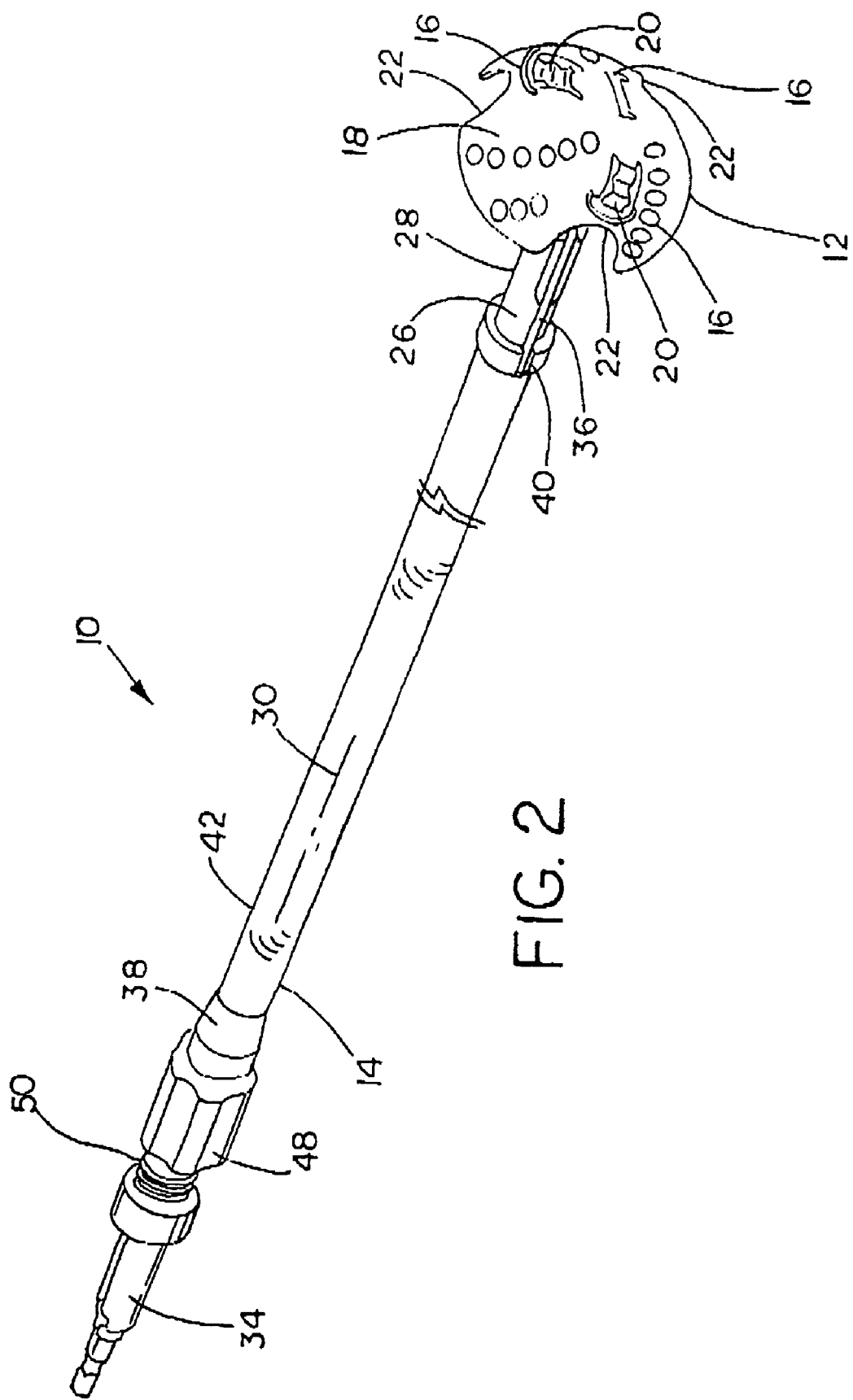
FIG. 2 is a perspective view of an embodiment of the orthopaedic reamer assembly of the present invention shown with the reamer in an operational position.
Figure 3:
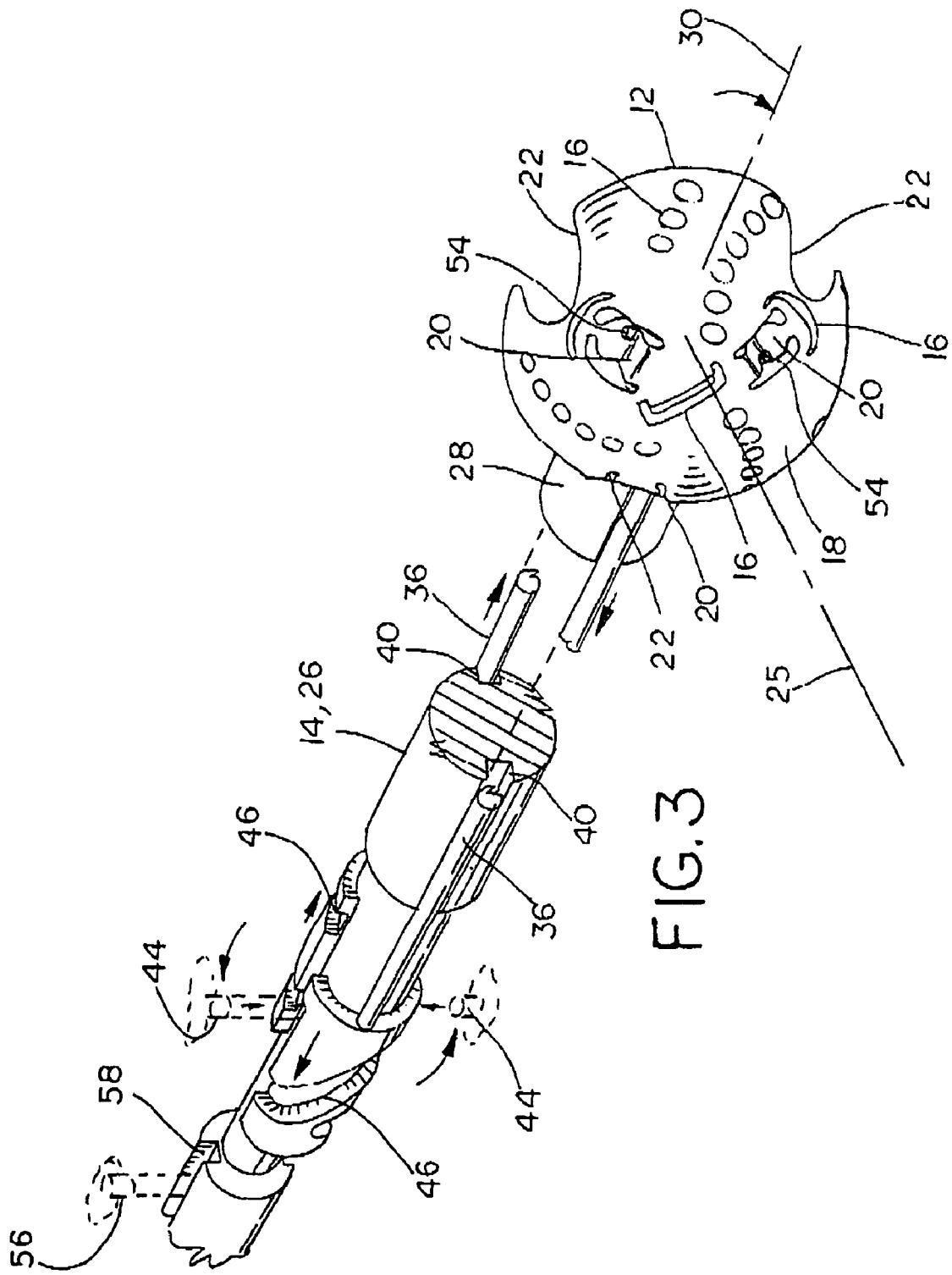
FIG. 3 is a fragmentary perspective view of an embodiment of the orthopaedic reamer assembly of the present invention shown with the reamer in an insertion or retraction position.
Figure 4:
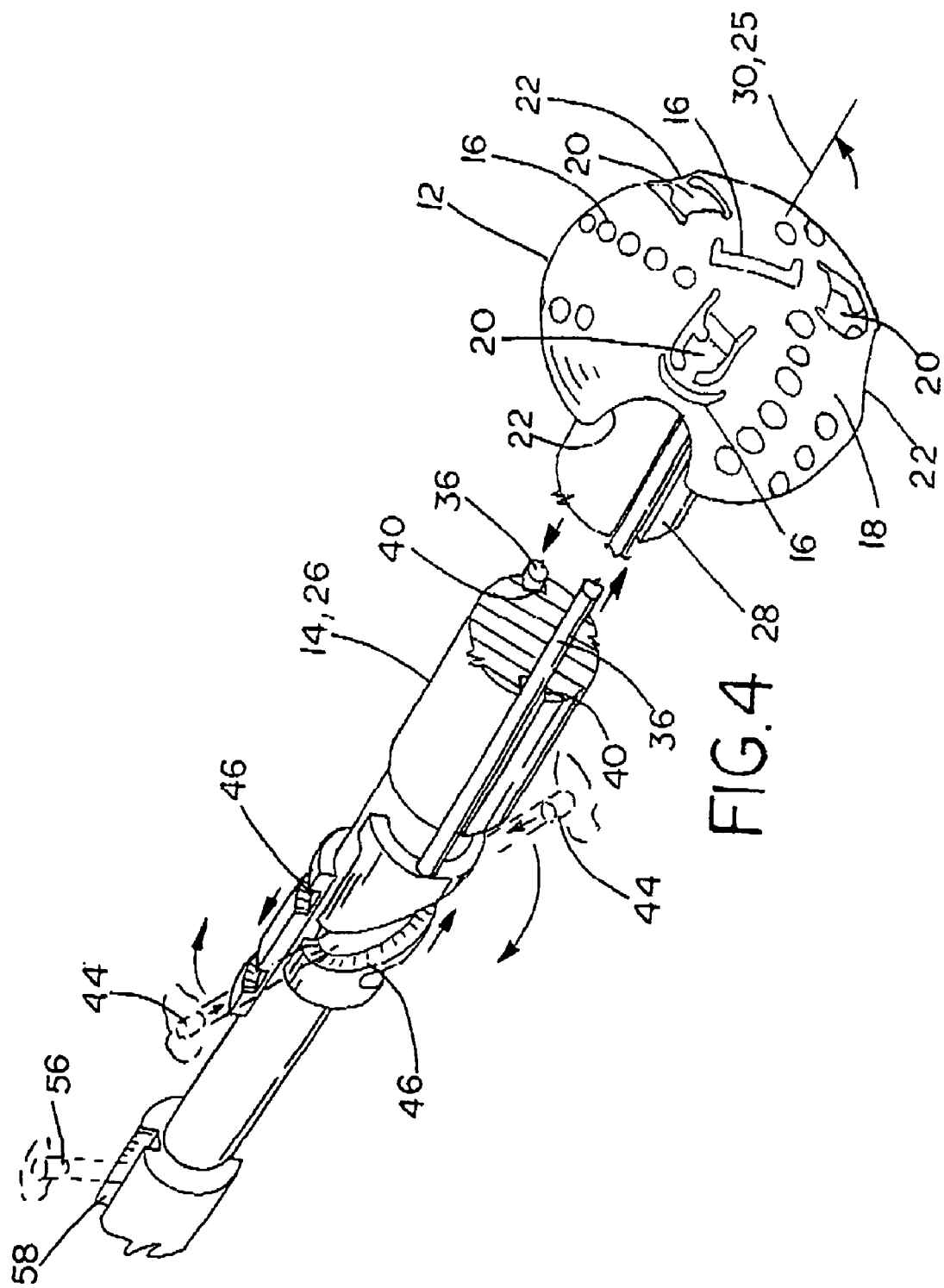
FIG. 4 is a fragmentary perspective view of an embodiment of the orthopaedic reamer assembly of the present invention shown with the reamer in an operational position.

Chuck 38 includes cam pins 44 on an inside surface of chuck 38 that engage cam raceways 46 on rods 36. When knob 48 is actuated towards resilient member 50 both rods 36 actuate towards proximal end 34 thereby pulling collar 52 away from head pins 54 and allowing either releasing attachment elements 20 of reamer 12, or attaching of reamer 12 via insertion of attachment elements 20. When knob 48 is both translated toward distal end 34 and rotated about longitudinal axis 30 each cam pin 44 actuates along a corresponding cam raceway 46 which pulls on one rod 36 and pushes on the other rod 36, which in turn, rotates drive head 32. Reamer 12 connected to drive head 32 rotates through approximately 90° and cutouts 22 allow reamer 12 to clear shaft 26 thereby rotating reamer 12 into an insertion or retraction position. Orthopaedic reamer assembly 10 presents a reduced profile to a surgical incision, approximately equal to the radius of reamer 12, and allowing for minimally invasive surgery. Translation and reverse rotation of knob 48 rotates reamer 12 into an operational position as shown in FIG. 2, for example, thereby giving the surgeon and patient the benefit of a full hemispherical reamer.

Chuck pins 56, of chuck 38, inserted into chuck grooves 58, in shaft 26, constrain chuck 38 from rotating relative to shaft 26 when turning knob 48 to actuate rods 36 and thereby rotate driver head 32 and reamer 12.

In use, reamer 12 is connected to driver 14 with longitudinal axis 30. Reamer 12 is rotated about axis 24 transverse to longitudinal axis 30. Orthopaedic reamer assembly 10 is inserted into an incision (not shown). Reamer 12 is reversely rotated thereby returning reamer 12 to an operational position. After the reaming operation is complete, reamer 12 is rotated to the low profile folded position and withdrawn from the incision.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer assembly, comprising:
   a reamer; and
   a driver including:
      a shaft including a distal end and a longitudinal axis; and
      a driver head connected to said distal end, said driver head foldable approximately 90° about an axis generally perpendicular to said longitudinal axis, said driver head detachably connected to said reamer; and
      at least one rod which folds said driver head, said at least one rod including a first end and a second end, said first end connected to said driver head, said second end connected to said shaft, said shaft including a peripheral surface and defining at least one longitudinal groove in said peripheral surface, and at least a part of said rod lies moveably within said at least one longitudinal groove.

2. The orthopaedic reamer assembly of claim 1, wherein said reamer includes a generally hemisperical shell with cutouts for clearance with said shaft.

3. The orthopaedic reamer assembly of claim 1 wherein said driver includes a knob, said at least one rod is actuated by said knob.

4. The orthopaedic reamer assembly of claim 1 wherein said driver includes a tube at least partially covering both said shaft and said at least one rod.

5. The orthopaedic reamer assembly of claim 4, wherein said tube includes at least one indicia that indicates at least one proper actuation of said orthopaedic reamer assembly.

6. The orthopaedic reamer assembly of claim 1 wherein said second end of said at least one rod includes at least one cam raceway.

7. The orthopaedic reamer assembly of claim 1, wherein said distal end includes a third end, a fourth end opposing said third end, and a single pivot axis, said third and fourth ends being generally parallel to each other, said single pivot axis disposed between said third and said fourth ends, said driver head disposed between and pivotally coupled with said third and fourth ends along said single pivot axis.

8. An orthopaedic driver, comprising:
   a shaft including a distal end and a longitudinal axis; and
   a driver head connected to said distal end, said driver head foldable approximately 90° about an axis generally perpendicular to said longitudinal axis, said driver head configured for detachable connection with an orthopaedic reamer; and
   at least one rod which folds said driver head, said at least one rod including a first end and a second end, said first end connected to said driver head, said second end connected to said shaft, said shaft including a peripheral surface and defining at least one longitudinal groove in said peripheral surface, and at least a part of said rod lies moveably within said at least one longitudinal groove.

9. The orthopaedic driver of claim 8, wherein said driver includes a knob, said at least one rod is actuated by said knob.

10. The orthopaedic driver of claim 8, wherein said driver includes a tube at least partially covering both said shaft and said at least one rod.

11. The orthopaedic driver of claim 10, wherein said tube includes at least one indicia that indicates at least one proper actuation of said orthopaedic driver.

12. The orthopaedic driver of claim 8, wherein said second end of said at least one rod includes at least one cam raceway.

13. The orthopaedic driver of claim 8, wherein said distal end includes a third end, a fourth end opposing said third end, and a single pivot axis, said third and fourth ends being generally parallel to each other, said single pivot axis disposed between said third and said fourth ends, said driver head disposed between and pivotally coupled with said third and fourth ends along said single pivot axis.

* * * * *